(12) United States Patent
Van Olmen

(10) Patent No.: US 12,222,296 B2
(45) Date of Patent: Feb. 11, 2025

(54) INSPECTION SYSTEM FOR QUALITY ANALYSIS OF A PRODUCT TO BE INSPECTED

(71) Applicant: Multiscan Technologies, S.L., Cocentaina (ES)

(72) Inventor: Simon Hendrik E. Van Olmen, Cocentaina (ES)

(73) Assignee: Multiscan Technologies, S.L., Cocentaina (ES)

( * ) Notice: Subject to any disclaimer, the term of this patent is extended or adjusted under 35 U.S.C. 154(b) by 161 days.

(21) Appl. No.: 17/916,620

(22) PCT Filed: Mar. 11, 2021

(86) PCT No.: PCT/ES2021/070177
§ 371 (c)(1),
(2) Date: Oct. 3, 2022

(87) PCT Pub. No.: WO2021/224517
PCT Pub. Date: Nov. 11, 2021

(65) Prior Publication Data
US 2023/0152240 A1 May 18, 2023

(30) Foreign Application Priority Data

May 5, 2020 (ES) ............................. ES202030393

(51) Int. Cl.
*G01N 21/88* (2006.01)
*G01N 21/958* (2006.01)
(Continued)

(52) U.S. Cl.
CPC ....... *G01N 21/8806* (2013.01); *G01N 21/958* (2013.01); *G01N 23/04* (2013.01);
(Continued)

(58) Field of Classification Search
CPC .. G01N 21/8806; G01N 21/958; G01N 23/04; G01N 23/083; G01N 2201/062; G01N 2223/421
See application file for complete search history.

(56) References Cited

U.S. PATENT DOCUMENTS 4,366,382 A 12/1982 Kotowski
5,603,413 A 2/1997 Mitchum, Jr.
(Continued)

OTHER PUBLICATIONS

International Search Report in PCT/ES2021/070177, mailed Jun. 4, 2021.
(Continued)

*Primary Examiner* — Hung V Nguyen
(74) *Attorney, Agent, or Firm* — Michael Best & Friedrich LLP

(57) ABSTRACT

The invention relates to an inspection system for quality analysis of a food product, comprising a conveyor for moving it to an inspection area, a lighting device consisting of LEDs that emit a light sequence directed towards the inspection area to light up the product by transmission, a linear camera with at least one line of pixels for collecting a plurality of images in each light sequence of the lighting device, and a focusing member for focusing the beam emitted by the lighting device. Advantageously, the lighting device is activated in a pulsed manner, generating a light sequence with at least two different illuminations, at least one of which is a transmission-pulsed illumination. The lighting device is aligned on the axis formed by the product to be inspected and the linear camera.

12 Claims, 6 Drawing Sheets

(51) Int. Cl.
G01N 23/04 (2018.01)
G01N 23/083 (2018.01)
G01N 33/00 (2006.01)
G01N 33/02 (2006.01)

(52) U.S. Cl.
CPC ....... *G01N 23/083* (2013.01); *G01N 33/0098* (2013.01); *G01N 33/025* (2013.01); *G01N 2201/062* (2013.01); *G01N 2223/421* (2013.01); *G01N 2223/646* (2013.01); *G01N 2223/652* (2013.01)

(56) References Cited

U.S. PATENT DOCUMENTS

| | | | | |
|---|---|---|---|---|
| 5,745,176 | A * | 4/1998 | Lebens | G01N 21/8806 348/370 |
| 8,355,581 | B2 * | 1/2013 | Noy | G01B 11/24 382/199 |
| 11,249,030 | B2 * | 2/2022 | Van Olmen | G01N 21/255 |
| 11,328,380 | B2 * | 5/2022 | Pinter | G06T 7/586 |
| 2008/0285030 | A1 | 11/2008 | Beltrandi | |
| 2010/0260378 | A1 | 10/2010 | Noy et al. | |
| 2017/0295323 | A1 | 10/2017 | Millar et al. | |

OTHER PUBLICATIONS

AnneMarie McCarthy et al., "LED-Based Collimating Line-Light Combining Freeform and Fresnel Optics", IEEE Photonics Journal, USA, vol. 10, No. 6, Dec. 1, 2018, pp. 1-13, total of 14 pages.

* cited by examiner

INSPECTION SYSTEM FOR QUALITY ANALYSIS OF A PRODUCT TO BE INSPECTED

CROSS REFERENCE TO RELATED APPLICATIONS

This application is the National Stage of PCT/ES2021/070177 filed on Mar. 11, 2021, which claims priority under 35 U.S.C. § 119 of Spanish Application No. P202030393 filed on May 5, 2020, the disclosure of which is incorporated by reference. The international application under PCT article 21(2) was not published in English.

OBJECT OF THE INVENTION

The present invention relates to a system for analyzing the quality of a product, for example, a food product, by means of lighting up said product by transmission, the system being provided with a lighting device consisting of LEDs which lights up the product, and a linear camera which captures the images of the light sequence which has gone through the product to be analyzed.

In this way, conveyance means move the product by means of a continuous forward advancement, with the illumination preferably being located below the conveyance means and the camera on the opposite side.

The object of the invention is to provide a system which enables a quick, complete or partial, analysis of the quality of products, detecting products which are defective, as well as the presence of foreign bodies.

BACKGROUND OF THE INVENTION

Systems which allow products to be inspected by means of using a light beam going through the product completely are known. One example of these systems is disclosed in patent document no. US2008285030, which describes an inspection system lighting by transmission.

This system is characterized by including a spectrometer which advantageously takes measurements across a broad spectrum, measuring the density of different wavelengths upon passing through the product. This measurement of the different wavelengths enables obtaining information about the internal quality of the products. One example of the application of this system is the determination of a food product's degrees Brix.

The drawback of the system disclosed in patent US2008285030 lies in the low acquisition speed and in the fact that it is a localized sensor. In other words, this system lights up the product entirely, not a smaller part thereof, so the product is observed as a whole, where possible partial defects of the product are diluted in the whole of the product.

U.S. Pat. No. 5,603,413 discloses a method and system for selecting optically transparent articles, specifically for selecting plastic articles. The system emits a polychromatic light beam through each article and the amount of light going through the article at certain wavelengths is detected by means of one or more linear cameras arranged opposite the light source.

The drawback of the system disclosed in U.S. Pat. No. 5,603,413 lies in the fact that the lighting system completely lights up the product, where partial defects or small differences in composition within one and the same product cannot be detected, but rather the system only serves for separating different products with a homogenous composition. Additionally, this system has a polychromatic light source and several linear cameras, with the resulting cost being higher than the system proposed in the present invention which includes a single linear camera.

Inspection systems which light up the product as a whole, diluting the presence of partial defects during detection, are known in the state of the art.

The need for automatic inspection systems which allow ensuring maximum quality of produced food products has been detected in the food industry sector. Specifically, inspection systems which are capable of eliminating small defects such as remnants of leaves in chopped strawberry or remnants of splinters in chopped peach, in addition to any other type of chopped fruits or vegetables, are required in the processed fruit and vegetable industry. Systems which analyze a product flow such as the one described using multiple linear cameras are known in the state of the art today; however, detection efficiencies are low, making it necessary to analyze the product several times, with a very high process cost and wastage.

Based on the foregoing, the applicant of the present patent has detected the need to offer a system which analyzes a product flow by transmission, lighting up the product to be inspected in a narrow line, that is, lighting up the product partially, enabling defects which affect the product to be inspected only partially, such as small remnants of leaves or remnants of pits in chopped fruits and vegetables, to be more precisely detected.

DESCRIPTION OF THE INVENTION

The inspection system proposed below solves the problems set forth above.

In this sense, the inspection system of the invention enables analyzing translucent products, that is, products through which light can pass.

Moreover, throughout the description, "product" refers to a flow of preferably food products which move continuously along the conveyance means, specifically small products and pieces, such as chopped fruits and vegetables.

Preferably, the semi-translucent product comprises a relatively small size. As a reference, products measuring a few mm to a few cm can be measured.

The product therefore moves along conveyance means, by means of a continuous forward advancement, through the inspection area. The arrangement of a lighting device and the linear camera must be arranged such that, when capturing the images of the light sequence on the product, the arrangement of the lighting device and the linear camera are located on opposite sides of the product to be analyzed.

As the product goes through the inspection area, the lighting device is activated in a manner that is synchronized with the acquisition of images by the linear camera, such that an image is formed by scanning the product as it goes through the inspection area. Preferably, the lighting device will be activated in a light sequence directed towards the inspection area such that the linear camera acquires one line for each activation of a specific illumination. The product advances on the conveyance means. Every time the product advances by a space corresponding to the size of a pixel, this light sequence will be executed, and images will be acquired, whereby an image of the product in consecutive lines will be obtained, that is, images corresponding to different illuminations will be obtained. This composite image can be readily decomposed with image processing, obtaining images corresponding to each illumination.

The light sequence is generated by the activation of the lighting devices. The lighting devices may consist of LEDs with a single specific wavelength, LEDs with several wavelengths, LEDs with a polychromatic spectrum (white light), or the combination of any of these, where transmission lighting devices, that is, any device located on the side opposite the linear camera, can be combined with devices located on the same side as the camera.

Therefore, in an embodiment option, the lighting device is located below the conveyance means, with the camera being located on the side opposite the lighting device with respect to the conveyance means.

In another embodiment option of the invention, the linear camera and the lighting device could be arranged forming an axis with the product to be analyzed, without the conveyance means being present, for example, performing the measurement in the area in which the product is in the air at the outlet of the conveyance means.

Optionally, the lighting device consists of LEDs that emit at at least two different wavelengths, focusing on the forward advancement direction of the conveyance means. In other words, they are two pulsed illuminations with different wavelengths focused on the Y axis (the axis of forward advancement). Therefore, light sequences which do not light up the inspection area simultaneously and light sequences that do, furthermore at different wavelengths, are generated.

In a preferred embodiment of the invention, the system includes a linear camera which allows images corresponding to the different illuminations of each light sequence to be acquired at a high speed.

Optionally, the linear camera may comprise a sensor with several lines of pixels in the forward advancement direction of the conveyance means. In this way, the linear camera with a sensor of several lines of pixels allows a filter for a specific wavelength to be arranged in each line of pixels, enabling images corresponding to different wavelengths to be acquired simultaneously, either by activating the illumination of LEDs with different wavelengths or by activating LEDs with a polychromatic spectrum. Therefore, the number of illuminations in each light sequence is reduced, where work can be performed with the conveyance means at a higher speed and/or where there is more image acquisition time per illumination, with the subsequent simplification of the lighting device.

In an optional embodiment of the invention, the inspection system includes an x-ray camera arranged close to the inspection area in the forward advancement direction, with the linear camera obtaining images of the product to be inspected by transmission and the x-ray camera obtaining x-ray attenuation images. Advantageously, the combination of the technologies used in the x-ray camera and the linear camera allows improved efficiency in defect detection since the information obtained from the analysis of one of the images can be used as an input element for the analysis of the second image. For example, the x-ray attenuation image provides information about the mass (thickness) of the product, which influences the attenuation of the light as it goes through the product.

Therefore, the x-ray camera captures the image of the product at a time before or after the linear camera captures the images. Capturing an optical image obtained by transmission and an x-ray attenuation image allows correlations to be made between the obtained images and the possibility of analyzing the product to be inspected with greater precision.

DESCRIPTION OF THE DRAWINGS

To complement the description made below and for the purpose of aiding to better understand the features of the invention according to a preferred practical embodiment thereof, a set of drawings is attached as an integral part of said description, wherein the following is depicted in an illustrative and non-limiting manner.

PREFERRED EMBODIMENT OF THE INVENTION

Figure 1:
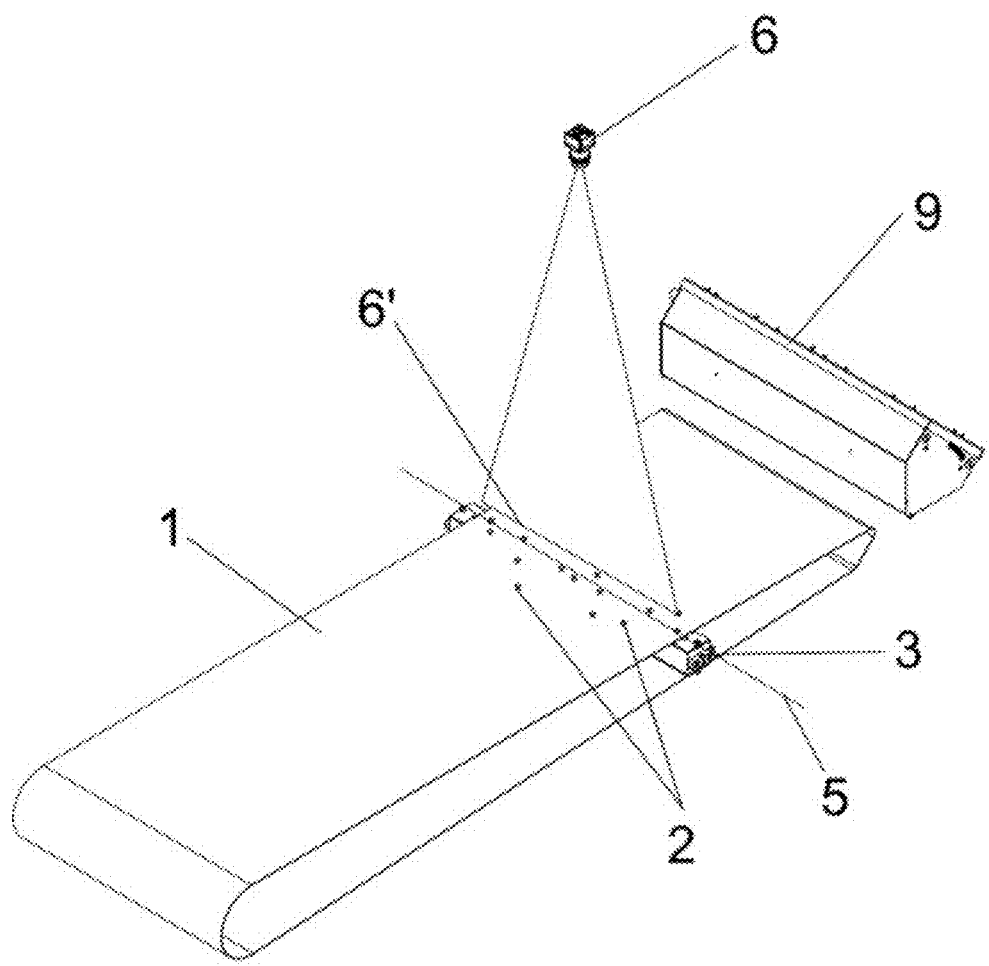
FIG. 1 shows a schematic perspective view of the inspection system for quality analysis of a product to be inspected, according to the description of the present invention.

FIG. 1 shown herein allows observing a general depiction of the inspection system object of the invention. Specifically, the inspection system for quality analysis of a product consists of the following elements:

Conveyance means (1) for moving the product (2) to be inspected to an inspection area (5). Specifically, the conveyance means (1), preferably a translucent belt, generate the movement of the product (2) by means of a continuous movement by forward advancement. The presence of a translucent belt enables the light beam which goes through the product to be analyzed to go through said belt.

A lighting device (3) consisting of LEDs (4) that emit a light sequence directed towards the inspection area (5), such that the light beam emitted by the LEDs (4) lights up the product (2) in the inspection area (5) by transmission.

A linear camera (6) with at least one line of pixels (6') for collecting a plurality of images in each light sequence of the lighting device (3).

Focusing means for focusing the beam emitted by the lighting device (3) and advantageously lighting up only a narrow line and prevent the presence of light reflected on the product which may reach the linear camera (6).

As seen in FIGS. 2 to 5, the light sequence is generated by the lighting device (3) where the LEDs (4) comprised in the lighting device (3) are arranged, preferably below the inspection area (5). In this way, the product (2) to be inspected advances forward along the belt (1) until reaching the inspection area (5) and the light beam emitted by the LEDs (4) lights up the product (2) by transmission precisely when the product goes through the inspection area (5).

The illumination is activated in a pulsed manner to light up the product (2) to be inspected. The light sequence can further include front illumination.

Specifically, the product (2) is lighted up with at least two different illuminations, at least one of which is by transmission, with the illumination being focused on the forward advancement direction of the conveyance means (1).

As shown in FIG. 1, when the product (2) to be inspected reaches the inspection area (5), the product (2) is lighted up by the lighting device (3) and the linear camera (6) scans the lighted-up product (2).

Therefore, in the continuous forward advancement of the belt, the linear camera captures product images line by line, by way of scanning. A light sequence consists of as many images as different illuminations there are. For example, in the case of a system with illumination at 850 nm and 660 nm, a light sequence in which illumination at 850 nm is first activated, acquiring a product image from one line, and in which illumination at 660 nm is subsequently activated, acquiring another product image from one line, is obtained. This action is performed for each forward advancement of the product flow corresponding to the size of one pixel.

That is, the linear camera (6) acquires more than one image of a pixel of the product (2) to be inspected for each forward advancement, specifically one image per illumination.

The images collected by the linear camera are sent to an automaton, and after analyzing the obtained images, the software sorts the product into a quality category.

Optionally, if the final inspected product (2) is not of the required quality, the automaton sends an order to an ejection device (9) which is installed downstream of the belt and enables products which do not meet the required quality to be rejected.

Figure 2:
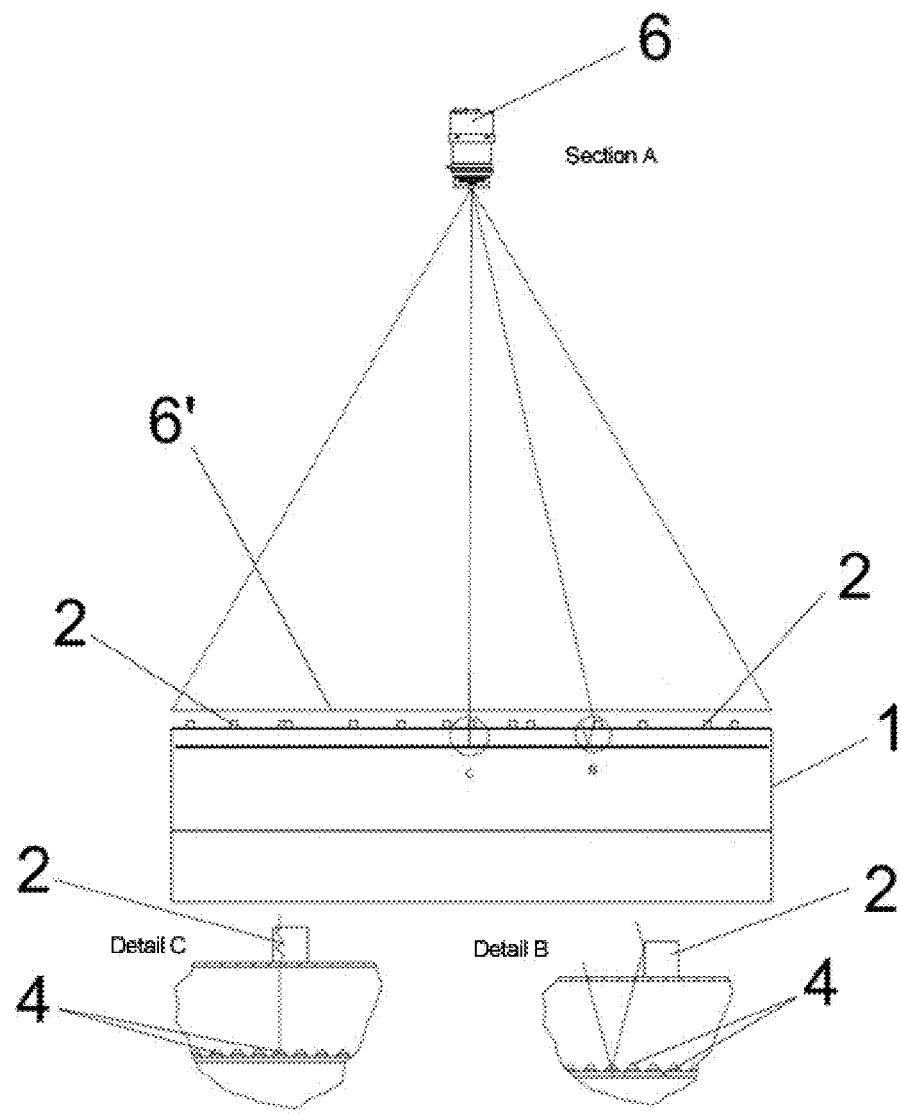
FIG. 2 shows a view and a detail of the cross-section of the inspection area of the system depicted in FIG. 1, in which the lighting device and how the light goes through or is reflected on the product to be inspected are further observed.

As seen in FIG. 2, the lighting device (3) is necessarily aligned on the imaginary axis formed by the product (2) to be inspected and the linear camera (6).

Detail C of FIG. 2 shows a case in which the light beam emitted by the LEDs (4) goes through the product (2) to be analyzed, said product being located in the ideal location for the linear camera (6) to capture its images, offering reliable results of the quality of the inspected product (2).

However, detail B of FIG. 2 depicts a case in which the product (2) is partially lighted up laterally, that is, the light beam emitted by the LEDs (4) does not go through the product (2), but rather is reflected directly towards the camera. This situation affects the precision of the analysis and must be avoided, given that the light which has gone through the product is not being analyzed in this case, producing an incorrect reading of the quality of the inspected product. Furthermore, it should be noted that this reflected illumination has a greater density than the illumination which has gone through the product, severely distorting quality analysis.

Figure 3:
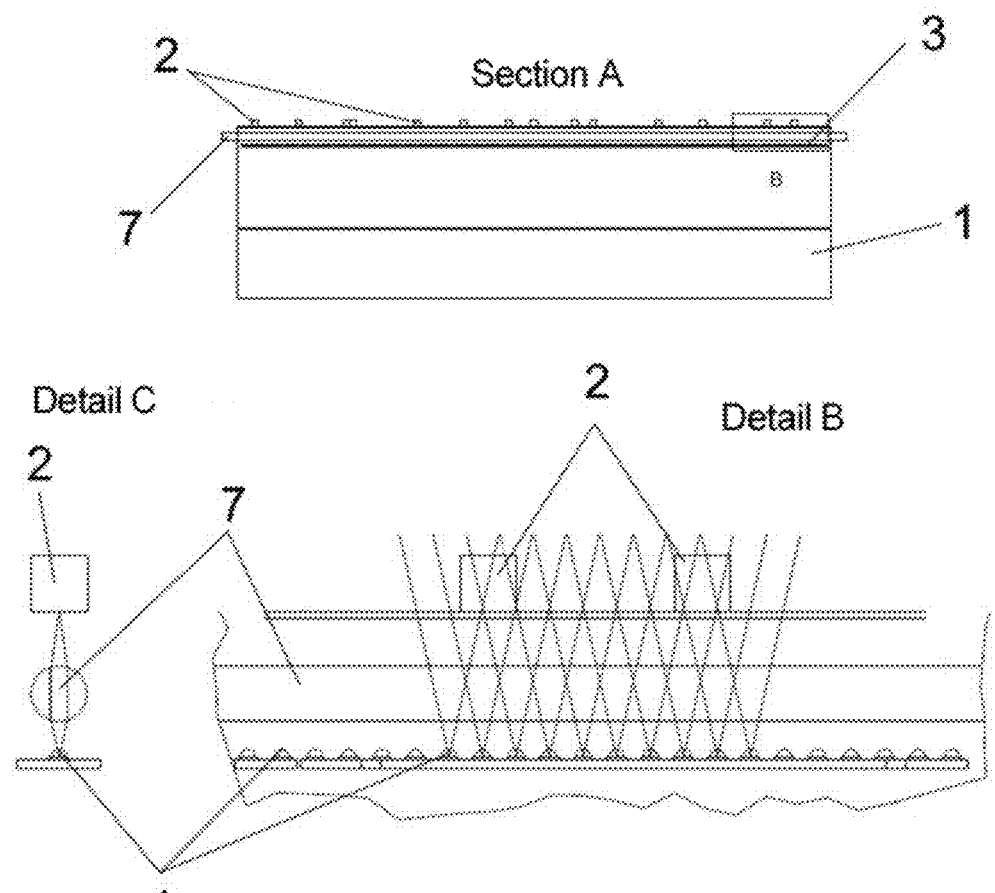
FIG. 3 shows a view and a detail of the cross-section of the inspection area of the inspection system according to the description of the present invention, in which an optical element is included for focusing the beam emitted by the lighting device in the forward advancement direction.

In the embodiment of the invention depicted in FIG. 3, the focusing means consist of a single cylindrical lens (7). Advantageously, since the system is configured with a single cylindrical lens (7), the light beam is focused on the forward advancement direction of the product (2), such that the cylindrical lens (7) takes in the light beam emitted by the LEDs (4) of the lighting system (3), focusing in one dimension, forming a straight narrow line that is aligned with the inspection area (5), as seen in section C of FIG. 3.

Preferably, the straight narrow line of focused illumination must have a width of less than 5 mm. Advantageously, by lighting up a smaller area of the product to be analyzed, more accurate information about the product is obtained.

For example, if the product to be analyzed comprises an area of one square centimeter and has a defect measuring 2×2 mm in the lower part, it means that the defect is located on the surface of the translucent product on the illumination side. Therefore, if the entire area of the product is lighted up, the amount of light which has gone through the defect is only 4%, but if a narrow area measuring 1 mm in width, with the help of a single cylindrical lens, is lighted up, the amount of light going through the defect will be 20%, thereby facilitating defect detection.

Figure 4:
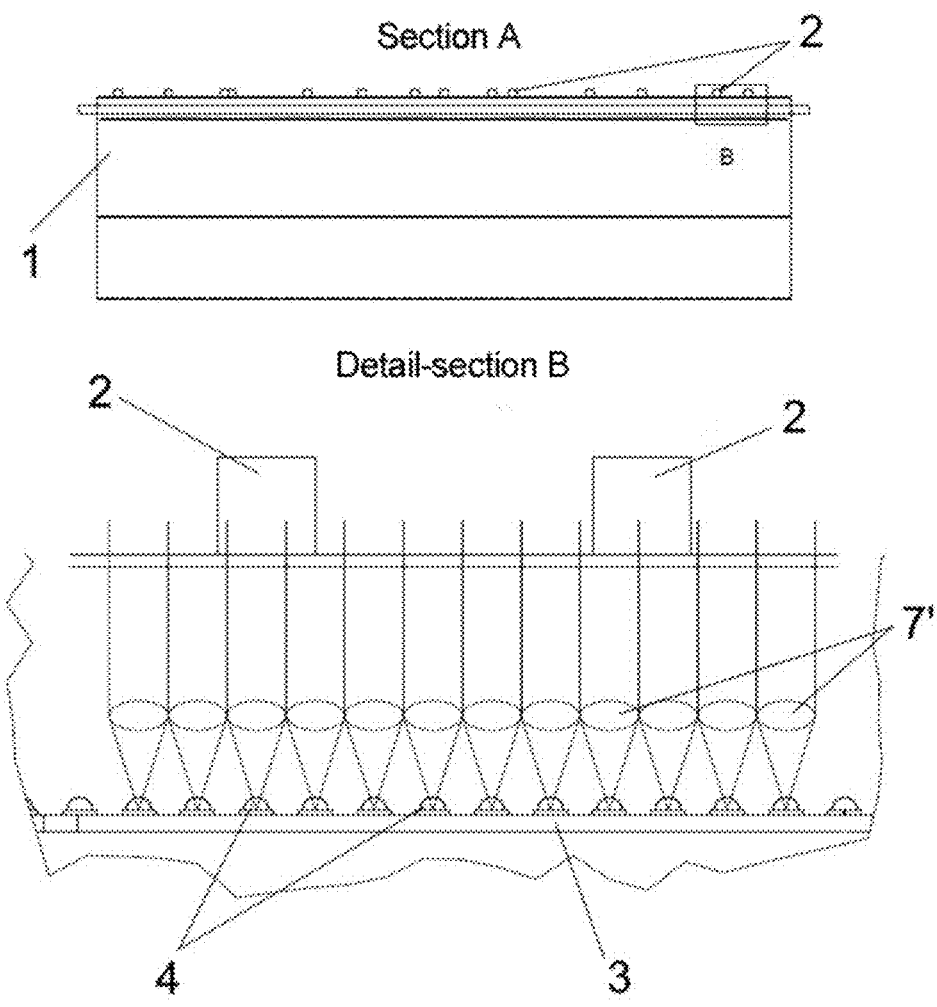
FIG. 4 shows a view and a detail of the cross-section of the inspection area of the inspection system according to the description of the present invention, in which an optical element is included for focusing the beam emitted by the lighting device in two directions.

In another embodiment of the invention depicted in FIG. 4, the focusing means consist of a plurality of independent lenses (7') for each LED (4). In this way, the inspection system of the invention is provided with as many independent lenses (7') as LEDs (4) comprised in the lighting device (3).

In this embodiment, since the focusing means consist of a plurality of independent lenses (7'), the light beam from the LEDs (4) is focused in two dimensions, one dimension being in a transverse direction with respect to the forward advancement direction of the belt (X) and the other dimension being in the forward advancement direction of the belt (Y).

Focusing the illumination in two directions by means of independent lenses (7') prevents the presence of light directly reflected on one side of the product to be inspected towards the camera (6).

In the embodiment depicted in both FIG. 2 and FIG. 3, the mentioned focusing means are arranged between the lighting device (3) and the inspection area (5) through which the product (2) to be inspected moves. In this way, focusing takes place before the light beam emitted by the LEDs (4) strikes the product (2).

Moreover, it should be indicated that the system of the invention may optionally comprise collimating means, preferably, by way of slits, not depicted in the figures. In this sense, in another embodiment of the invention, the inspection system first allows focusing the light beam emitted by the lighting device (3), and then collimation takes place by means of the slits, thereby achieving the narrowing of the beam which strikes the product (2) to be inspected and analyzed.

It should be noted that the lighting system is less efficient if the light beam is collimated, but not focused.

Figure 5:
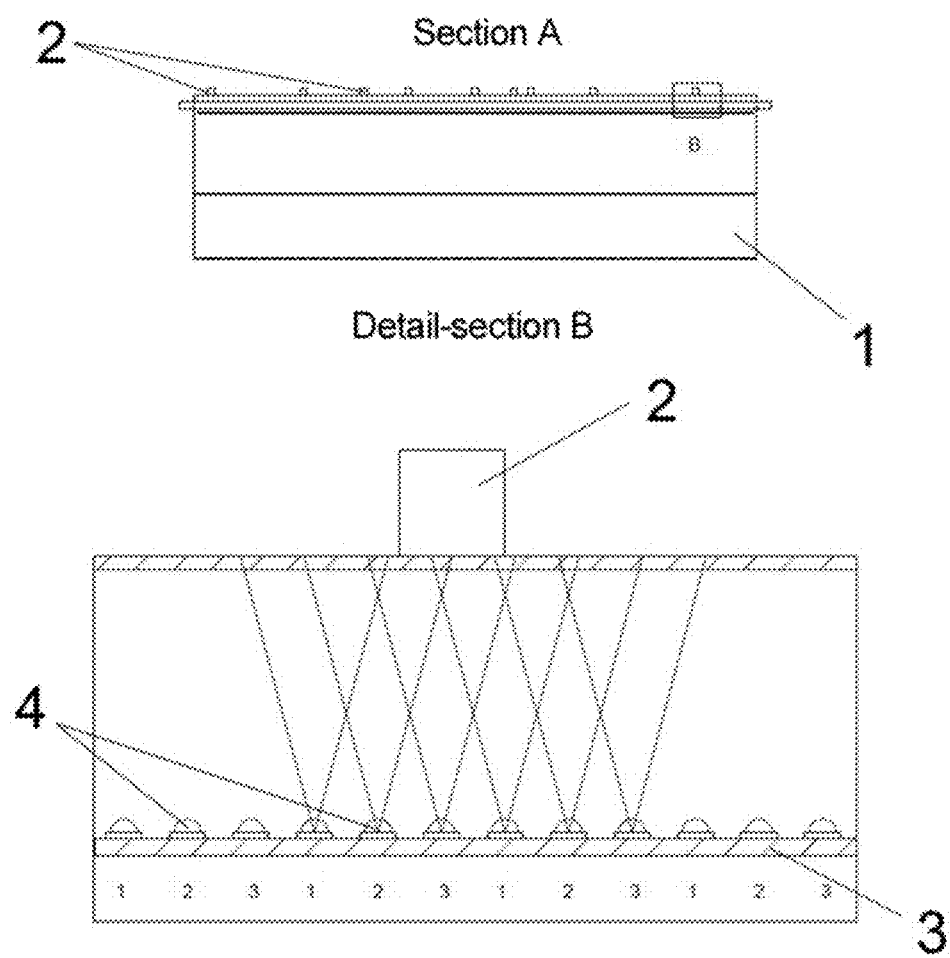
FIG. 5 shows a view and a detail of the cross-section of the inspection area of the inspection system, in which the LEDs lighted up at different times of the light sequence are depicted.

Moreover, the lighting devices (3) can be programmed, lighting up in groups at different times. Therefore, as depicted in FIG. 5, the LEDs (4) of the lighting device (3) light up by transmission in one and the same wavelength and are activated partially, i.e., in parts, in a transiently alternating manner in a light sequence; in other words, not all the LEDs (4) are activated at the same time.

For example, only even-numbered LEDs (4) would be activated and not odd-numbered LEDs (4) so as not to produce direct reflected light. The odd-numbered LEDs (4) would be activated later. In this way, a sequence with two illuminations by transmission, where each of them lights up a part of the inspection area, would be obtained. The analysis algorithm of the image would then recompose the image of the product to be inspected using, from both illuminations, only that part in which the illumination was activated, thereby obtaining the complete image by transmission. Therefore, reflected light can be avoided without having to use individual lenses. The same scheme can be repeated by activating, for example, one LED out of every three or four LEDs, whereby less reflected light would still be obtained with a sequence of three or four illuminations.

The advantage of activating the LEDs (4) in an alternating manner is to prevent the generation of direct reflected light.

Figure 6:
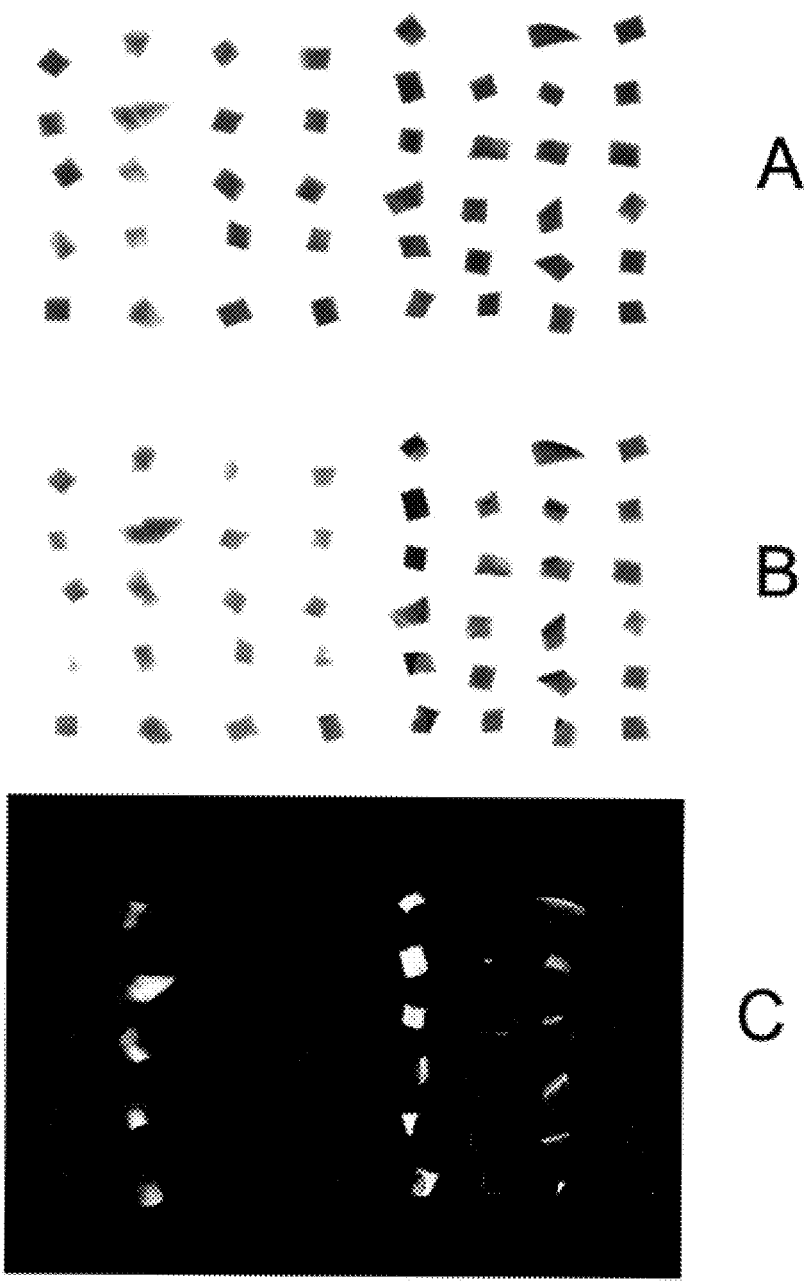
FIG. 6 shows the images obtained by LED transmission at 850 nm (detail A), 660 nm (detail B), and the chlorophyll index (detail C) calculated based on images A and B above.

Moreover, FIG. 6 allows verifying the results obtained with the inspection system of the invention when the lighting device emits a pulsed illumination with more than one wavelength, wherein at least one of the emitted wavelengths comprises a range of 650~690 nm and the other one is in the range of 800~940 nm. Advantageously, this configuration and emission in a range of 650-690 nm allows measuring the absorption of chlorophyll present in the product to be inspected. In this way, when the product has a leaf adhered thereto or is more unripe, the presence of the leaf or unripeness can be detected since the wavelength of 650~690 nm going through the product at that point (with leaves or unripened area) will be more attenuated in comparison with the length of 800~940 than a product that comprises no leaves or is ripe. The different signal attenuation of the wavelength of 650~690 nm is due to the absorption generated by chlorophyll.

Therefore, FIG. 6 shows the images of a plurality of pieces of fruit which have been obtained by transmission of the LED beam emitted at a wavelength of 850 nm (detail A) and 660 nm (detail B).

The chlorophyll index obtained in detail C is calculated based on details A and B. In this sense, FIG. 6 clearly shows in detail C the products and/or product parts containing chlorophyll, corresponding to those elements that are lighted up the most. Meanwhile, those products and/or product parts not comprising chlorophyll are darkened in detail C.

Lastly, it should be indicated that for any preferred embodiment of the invention, the inspection system includes an ejection device (9) to allow sorting, wherein the ejection device (9) receives the order according to the instructions sent by the automaton.

The invention claimed is:

1. An inspection system for quality analysis of a translucent product to be inspected, comprising:
   a conveyor for moving the translucent product to be inspected through an inspection area, generating the movement thereof,
   a lighting device consisting of LEDs that emit a light sequence directed towards the inspection area, such that a light beam emitted by the LEDs lights up the translucent product in the inspection area by transmission of the light beam through the translucent product,
   a linear camera with at least one line of pixels and being configured for collecting a plurality of images in each light sequence of the lighting device, the images being obtained by transmission of the light beam emitted by the lighting device upon passage of the translucent product to be inspected,
   focusing means for focusing the beam emitted by the LEDs,
   wherein the lighting device is configured to be activated in a pulsed manner, generating a light sequence, partially lighting up the translucent product with at least two different illuminations to provide a lighted-up translucent product, at least one of which is a pulsed illumination going through the translucent product, with the pulsed illumination being focused on a forward advancement direction of the conveyor;
   wherein the linear camera is configured to scan the lighted-up translucent product in the inspection area such that the linear camera acquires more than one image of a pixel of the lighted-up translucent product for each forward advancement; and
   wherein the lighting device is aligned on an axis formed by the translucent product to be inspected and the linear camera, with the lighting device and the linear camera being arranged on opposite sides of the translucent product.

2. The inspection system for quality analysis of a translucent product to be inspected according to claim 1, wherein the conveyor is a translucent conveyor, and wherein the LEDs of the lighting device are arranged below the translucent conveyor such that the light beam goes through the translucent product, lighting up the inspection area through which the translucent product passes.

3. The inspection system for quality analysis of a translucent product to be inspected according to claim 2, wherein the light beam which lights up the inspection area comprises a width of less than 2 mm.

4. The inspection system for quality analysis of a translucent product to be inspected according to claim 2, wherein the focusing means for focusing the beam emitted by the LEDs consist of a single cylindrical lens.

5. The inspection system for quality analysis of a translucent product to be inspected according to claim 2, wherein the focusing means for focusing the beam emitted by the LEDs consist of independent lenses for each LED, such that the system is provided with as many independent lenses as LEDs comprised in the lighting device, such that the illumination is focused in two dimensions, one dimension being in a transverse direction with respect to a forward advancement direction of the conveying means and the other dimension being in the forward advancement direction of the conveying means.

6. The inspection system for quality analysis of a translucent product to be inspected according to claim 1, further comprising a collimator for the narrowing of the light beam.

7. The inspection system for quality analysis of a translucent product to be inspected according to claim 1, wherein the LEDs comprised in the lighting device emit in at least two different wavelengths focused on a forward advancement direction of the conveyor and lighting up in an alternating manner.

8. The inspection system for quality analysis of a translucent product to be inspected according to claim 1, further comprising an ejection device to allow sorting the translucent product to be inspected.

9. The inspection system for quality analysis of a translucent product to be inspected according to claim 1, wherein the linear camera has a sensor of more than one line of pixels.

10. The inspection system for quality analysis of a translucent product to be inspected according to claim 1, wherein the lighting device is configured to light up in one and the same wavelength and is activated in parts, in an alternating manner in the light sequence.

11. The inspection system for quality analysis of a translucent product to be inspected according to claim 1, wherein the lighting device is configured to emit a pulsed illumination with more than one wavelength, wherein at least one of the emitted wavelengths comprises a range of 650~690 nm.

12. The inspection system for quality analysis of a translucent product to be inspected according to claim 1, further comprising an x-ray camera arranged close to the inspection area, with the linear camera obtaining images of the translucent product to be inspected by transmission and the x-ray camera obtaining x-ray attenuation images.

* * * * *